United States Patent [19]
Raphael, III et al.

[11] Patent Number: 4,832,694
[45] Date of Patent: May 23, 1989

[54] PROGRAMMED ACTION HYPODERMIC SYRINGE

[76] Inventors: Julian J. Raphael, III, Cranberry Creek Estates, Box 45, Cresco, Pa. 18326; Julian J. Raphael, II, 1600 Lehigh Pkwy. East, Allentown, Pa. 18103; Sheila R. Raphael, Cranberry Creek Estates, Box 45, Cresco, Pa. 18326; Besse Raphael, 1600 Lehigh Pkwy. East, Allentown, Pa. 18103

[21] Appl. No.: 153,809
[22] Filed: Feb. 8, 1988
[51] Int. Cl.$^4$ ............................................. A61M 5/00
[52] U.S. Cl. ........................................ 604/110; 604/208
[58] Field of Search ............... 604/110, 111, 207, 208, 604/209, 210, 218, 187, 220, 228; 222/153, 386

[56] References Cited

U.S. PATENT DOCUMENTS

| | | | |
|---|---|---|---|
| 320,261 | 6/1885 | Laflin | 604/210 |
| 1,393,720 | 10/1921 | Lomas et al. | 604/210 |
| 2,648,334 | 8/1953 | Brown et al. | 604/208 |
| 3,478,937 | 11/1969 | Solowey | 222/386 |
| 3,667,657 | 6/1972 | Chiquiar-Arias | 222/541 |
| 3,747,812 | 7/1973 | Karman et al. | 604/110 |
| 3,938,505 | 2/1976 | Jamshidi | 604/210 |
| 3,951,146 | 4/1976 | Chiquiar-Arias | 604/110 |
| 3,998,224 | 12/1976 | Chiquiar-Arias | 604/110 |
| 4,026,287 | 5/1977 | Haller | 604/110 |
| 4,188,950 | 2/1980 | Wardlaw | 604/110 |
| 4,233,975 | 11/1980 | Yerman | 604/110 |
| 4,367,738 | 1/1983 | Legendre et al. | 604/110 |
| 4,386,606 | 6/1983 | Tretinyak et al. | 604/220 |
| 4,391,272 | 7/1983 | Staempfli | 604/110 |
| 4,391,273 | 7/1983 | Chiquiar-Arias | 604/110 |
| 4,475,905 | 10/1984 | Himmelstrup | 604/208 |
| 4,493,703 | 1/1985 | Butterfield | 604/110 |
| 4,610,668 | 9/1986 | Fleig | 604/208 |
| 4,634,428 | 1/1987 | Cuu | 604/110 |
| 4,650,468 | 3/1987 | Jennings, Jr. | 604/110 |
| 4,687,467 | 8/1987 | Cygielski | 604/110 |
| 4,699,614 | 10/1987 | Glazier | 604/110 |

Primary Examiner—Stephen C. Pellegrino
Assistant Examiner—Ralph Lewis
Attorney, Agent, or Firm—Steele, Gould & Fried

[57] ABSTRACT

A programmed action hypodermic syringe includes a syringe barrel having at least one pin protruding into the bore of the barrel. A plunger is adapted to travel through the bore and has, on its exterior surface, at least one longitudinal tracking groove defining relative motion of the pin. The tracking groove has a continuous cam side allowing unlimited travel of the pin along a complete fill or drain stroke. Opposite the continuous cam side is a discontinuous cam side defining traps for the pin should the user reverse directions before completing the fill or drain stroke. Two tracking grooves are preferably provided to define a complete allowed path along a fill tracking groove and a drain tracking groove. These two grooves converge near an end of the plunger adjacent a fluid content chamber of the syringe barrel. The sides of the confluence are configured such that when the pin reached the confluence, that is at the point of passing from the completely filled position to the initial drain position, the pin moves by cam action into the drain tracking groove.

26 Claims, 3 Drawing Sheets

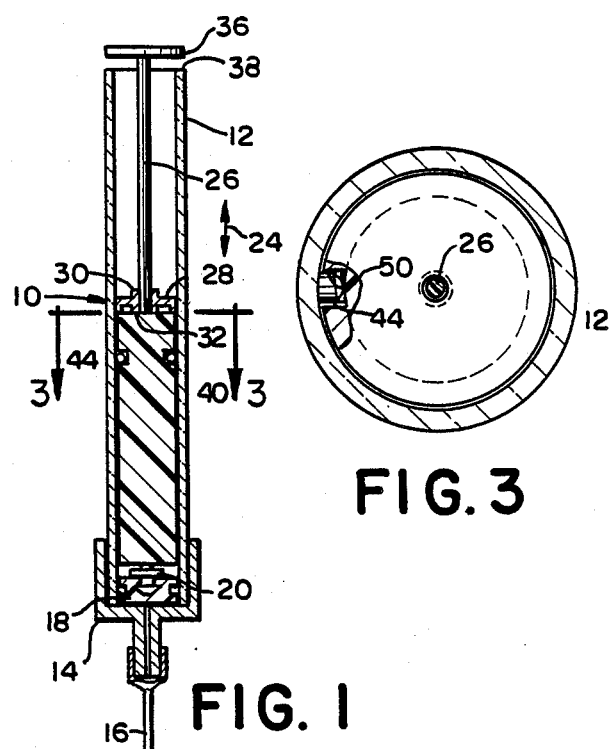
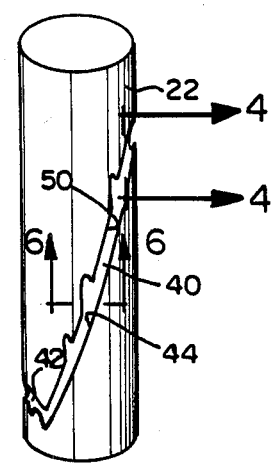
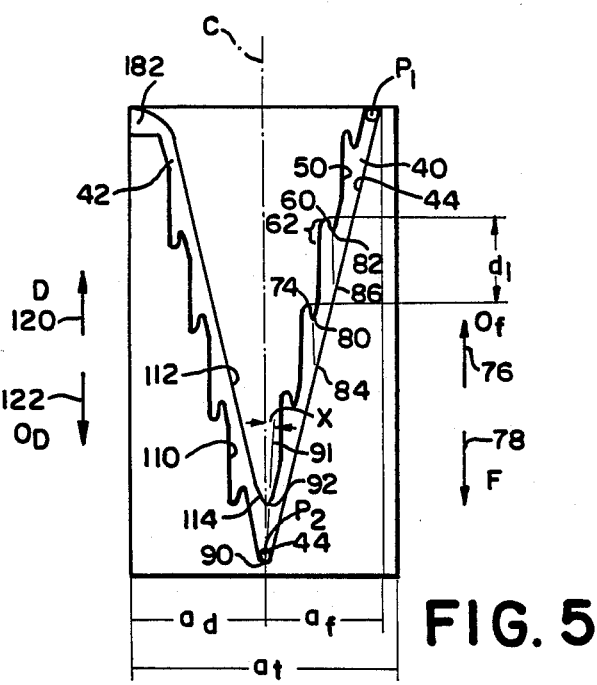

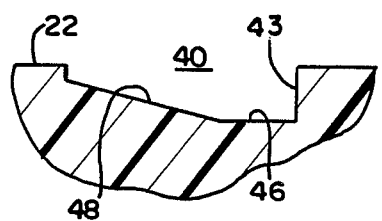
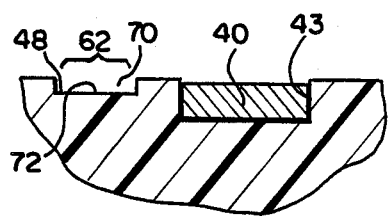
FIG. 4   FIG. 6
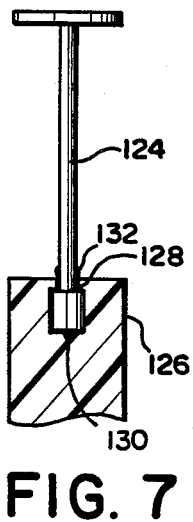
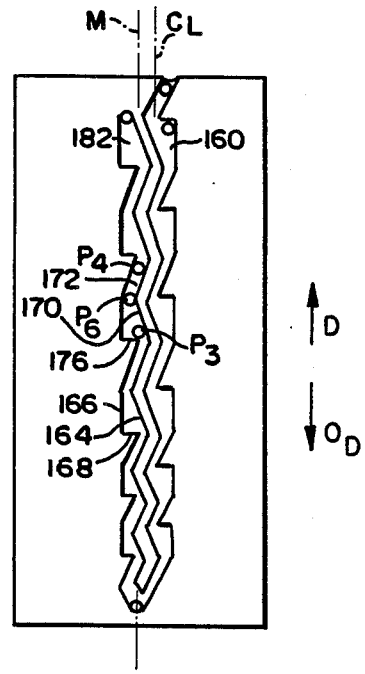
FIG. 7   FIG. 8

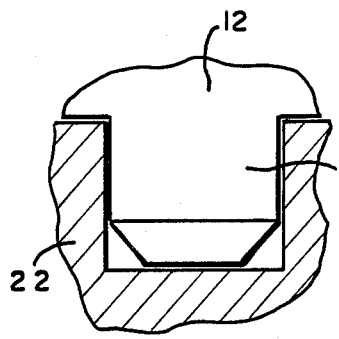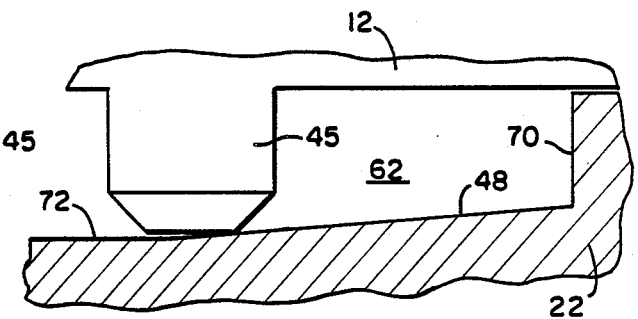
FIG. 9a          FIG. 9b
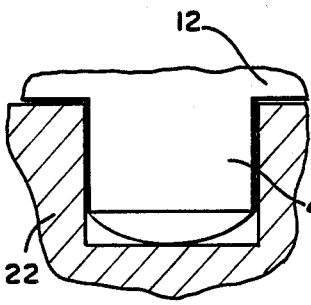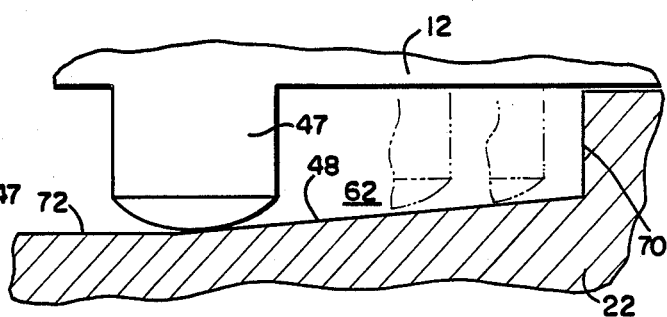
FIG. 10a         FIG. 10b
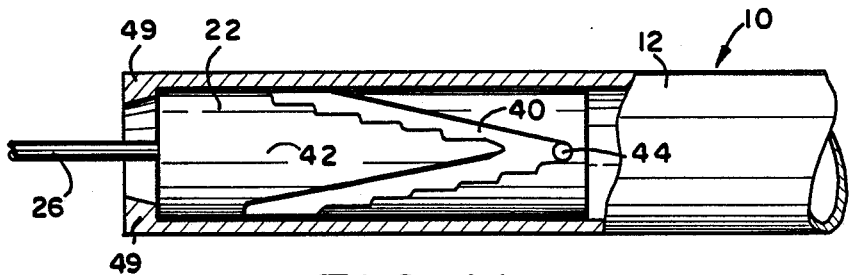
FIG. 11

PROGRAMMED ACTION HYPODERMIC SYRINGE

BACKGROUND OF THE INVENTION

The present invention relates to a programmed action hypodermic syringe wherein, in one embodiment, the syringe can only be filled by unidirectional plunger motion in a filling direction along the axis (movement in the opposite direction being precluded until the fill stroke is completed) and thereafter, the syringe can only be drained or emptied by unidirectional plunger motion in a draining direction (plunger movement being precluded in a direction opposite to the draining longitudinal direction).

It is desirable to have a hypodermic syringe that can only be filled once and/or drained once after which the syringe is rendered non-reusable and therefore fully disposable. Various devices for this purpose have been proposed. U.S. Pat. No. 4,699,614 to Glazier shows one form of non-reusable syringe. The Glazier syringe includes a hollow, cylindrical, plunger barrel or actuator having a zig-zag Z-shaped channel cut in the interior surface thereof. A plunger is actuated by the plunger barrel by moving a stem with radially protruding pins that cooperate with the channel in the plunger barrel. The plunger itself moves in a syringe barrel. To fill the Glazier syringe, at least one pin moves to a defined position in the Z-shaped channel and when so positioned movement of the plunger barrel with respect to the syringe barrel in an outboard direction causes the plunger, via the then-engaged pin and plunger stem, to fill the syringe barrel. During a subsequent ejection or drain mode, longitudinally inboard movement of the plunger barrel causes abutment of the pin against an opposing side of the Z-shaped channel and causes the pin to move along a channel to another defined pin position in the Z-shaped channel whereupon the pin and plunger engage for movement inboard. Further longitudinal inboard movement of the plunger barrel thus causes the plunger to move towards the closed end of the syringe, draining the syringe barrel. If the plunger barrel is thereafter moved longitudinally outboard, the pin follows a third leg of the Z-shaped channel that opens at the end of the plunger barrel such that when the plunger barrel is retracted after a use, the pin leaves the open end of the Z-shaped channel, the plunger is thereby disengaged, remaining in the fully drained position in the syringe barrel, and the syringe becomes inoperable.

The Glazier is limited to one filling and discharging cycle only if the fill and discharge strokes exceed the length of the Z-shaped channel. The syringe can be re-used an indefinite number of times if the stroke is kept shorter than the channel thereby avoiding release of the pin. If the channel length is any substantial portion of a full stroke, the syringe is not strictly non-reusable as a practical matter, but is only reusable in short strokes. It may also be possible to defeat the device by exerting excessive force.

The Glazier device depends on relative motion between the barrel, which is manually operated by the user, and the plunger seal assembly, to which the pin is fixed. Therefore the user perceives a lost motion when the plunger moves but the plunger seal does not move. This lost motion detracts from the precision of operation as perceived by the user.

U.S. Pat. No. 4,493,703 to Butterfield discloses a hypodermic syringe cartridge with a non-retractable drive piston. The piston includes at least two circumferential grooves in its exterior and the syringe barrel has a plurality of radially inward protruding stop edges that prohibit the withdrawal of the plunger when the stop edges lock in the circumferential channels. A number of such ratchet-like structures have been proposed. Typically, the ratchet structures prevent retraction of the plunger per se, and thus interfere with a syringe filling operation involving retraction.

U.S. Pat. No. 4,391,272 to Staempfli discloses a disposable syringe having similar locking characteristics as described with respect to Butterfield. U.S. Pat. No. 4,367,738 to Legendre et al. discloses a plunger having a plunger stem with a plurality of legs extending both longitudinally outboard and radially outward of a plunger stem. These legs lock with an interior stop surface in the syringe barrel. U.S. Pat. No. 3,478,937 to Solowey discloses a disposable syringe having a locking mechanism with feet that spring outward from the plunger stem. U.S. Pat. No. 4,233,975 to Yerman discloses a single use syringe having a separate blocking plunger that is actuated when the main syringe plunger is in the completely drained position. U.S. Pat. No. 4,391,273 to Chiquiar-Arias discloses a disposable syringe having a plunger with a circumferential groove and a plunger barrel having a inwardly protruding locking pin. U.S. Pat. No. 4,650,468 to Jennings, Jr., discloses a medical syringe having a circumferential groove on the plunger and a radially protruding annular ring in the syringe barrel. U.S. Pat. No. 4,634,428 to Cuu discloses a cover for a disposable syringe. U.S. Pat. No. 4,687,467 to Cygielski discloses a non-reusable medical syringe that destroys the syringe piston after use. U.S. Pat. No. 4,188,950 to Wardlaw discloses a disposable syringe that includes a dismountable end piece that bends the needle. U.S. Pat. No. 3,998,224 to Chiquiar-Arias discloses a disposable syringe utilizing a circumferential channel on the plunger and an annular ring extending inward to the syringe barrel. U.S. Pat. No. 3,747,812 to Karman, et al. discloses a disposable syringe that destroys the end of the syringe barrel. U.S. Pat. No. 3,667,657 to Chiquiar-Arias and U.S. Pat. No. 3,951,146 to Chiquiar-Arias also discloses a disposable syringe that destroys the end of the syringe barrel after use. U.S. Pat. No. 4,026,287 to Haller discloses a syringe having a plunger body with extending screw threads on its piston face that mate with complementary thread channels in the base of the syringe barrel.

OBJECTS OF THE INVENTION

It is an object of the present invention to provide a programmed action single use or disposable syringe.

It is another object of this invention to provide a syringe wherein the longitudinal action of the syringe can be programmed dependent upon grooves or channels present in the exterior surface of the plunger.

It is a further object of the present invention to provide a syringe that can be configured only to drain fluid from the syringe barrel, that is, the syringe can only be used to dispense fluid and thereafter cannot be filled again.

It is another object of the present invention to provide a syringe that can be programmed only to fill the syringe barrel and cannot be discharged until the filling is complete.

It is an additional object of the present invention to provide a syringe that prohibits longitudinal movement of the plunger in an opposing, non-programmed longitudinal direction and if excessive force in that non-programmed direction is applied to the syringe, the syringe is destroyed by jamming of the movable parts and ultimately by breakage or deformation of the plunger stem.

It is a further object of the present invention to provide a syringe that is manufactured more easily than prior art disposable syringes.

SUMMARY OF THE INVENTION

In one embodiment, the programmed action hypodermic syringe includes a syringe barrel having at least one pin protruding into the bore of the barrel. A plunger is adapted to travel through the bore. The plunger has, on its exterior surface, at least one longitudinal tracking groove within which the pin travels during relative movement between the plunger and the barrel. The tracking groove has a continuous cam side for unlimited cam action travel of the pin in the groove in, for example, a drain longitudinal direction. Opposite the continuous cam side is a discontinuous cam side for limited cam action travel in the opposite longitudinal direction with respect to the drain direction. The continuous cam side is angularly disposed with respect to the generally longitudinal movement of the plunger such that the pin, in the programmed travel direction, acts as a cam follower riding on the continuous cam side of the groove and rotates the plunger with respect to the barrel. If the plunger is moved in the opposite direction, that is the direction not programmed, the pin moves substantially longitudinally in the groove and is trapped or stopped by the discontinuous cam side of the groove. Another embodiment of the invention utilizes two tracking grooves, a fill tracking groove and a drain tracking groove. These two grooves converge or have a confluence near an end of the plunger adjacent a fluid content chamber of the syringe barrel. The sides of the confluence are specially configured such that when the pin moves across the confluence, that is from the completely filled position to an initial draining position, the pin is moved by cam action into the drain tracking groove. The configuration of the barrel is such that the barrel structure prevents the plunger from being retracted to the point that the pin at the confluence of the tracking grooves abuts the end of the groove. Therefore, the pin cannot be sheared off by fully retracting the pin and applying excessive force.

BRIEF DESCRIPTION OF THE DRAWINGS

Further objects and advantages of the present invention can be found in the detailed description of the preferred embodiments when taken in conjunction with the accompanying drawings in which:

FIG. 1 illustrates a cross-sectional view of the programmed action hypodermic syringe in a completely drained position in accordance with the present invention;

FIG. 2 is a perspective view of the plunger having a fill tracking groove and drain tracking groove;

FIG. 3 is a cross-sectional view of the syringe barrel showing the radially projecting pin;

FIG. 4 is a partial, cut-away view of tracking groove and the adjacent portion of the plunger as shown in FIG. 2;

FIG. 5 is a plan view of the fill and drain tracking grooves that are present on the exterior surface of the plunger;

FIG. 6 is a partial, cut-away view of the pin trap from the perspective of section line 6'—6" in FIG. 2;

FIG. 7 illustrates a partial, diagrammatic view of the plunger and plunger stem; and FIG. 8 is a plan view of fill and drain tracking grooves in accordance with a further embodiment of the present invention.

FIGS. 9a, 9b, 10a and 10b are partial section views of alternative pin shapes engaging in tracking groove pin traps; and FIG. 11 is a partial cut-away section view showing the plunger and pin at full retraction.

DETAILED DESCRIPTION OF THE PREFERRED EMBODIMENTS

The present invention relates to a programmed action hypodermic syringe.

FIG. 1 is a cross-sectional view of hypodermic syringe 10. Syringe 10 is preferably molded plastic and includes syringe barrel 12 and needle bushing 14 permanently mounted on one end of the barrel, for example by adhesive or heat welding. Needle 16 is mounted to needle bushing 14. A fluid content chamber 18 is defined by piston face 20 of plunger 22. Plunger 22 travels longitudinally in the interior of syringe barrel 12 as shown by double headed arrow 24. Downward motion of plunger 22 drains fluid from chamber 18 through needle 16 and upward motion of plunger 22 causes a filling of fluid chamber 18. These two movements are longitudinal movements and are referenced to the axis of the syringe 10. Plunger 22 is moved with respect to barrel 12 by plunger stem 26 acting on end 28 of the plunger remote from fluid chamber 18. Plunger stem 26 is freely rotatably but axially fixed to plunger 28. Stem stops 30 and 32 can be provided for this purpose above and below endwall 34 at plunger end 28. Therefore, plunger 22 cannot be rotated by rotation of plunger handle 36 attached to the outboard end of plunger stem 26. The term "outboard" refers to items or movements causing a specified item to move beyond the interior of barrel 12. "Inboard" movement refers to the specified item moving into barrel 12. Plunger 22 is shown as a solid, elongated cylinder in FIG. 1 (and partly in FIG. 7). The plunger may also be substantially hollow. Likewise, the various components may be made of metal, glass or other materials rather than plastic, as illustrated herein. The claims appended hereto are meant to cover these and other modifications.

Plunger 22 includes, in this embodiment, two tracking grooves define a path dimensioned to receive a pin. A fill tracking groove guides the pin in one direction and a drain tracking groove guides the pin in the other direction. At least one groove, and preferably both, have a plurality of pockets that will capture the pin if moved opposite a programmed direction and obstruct further operation. Barrel 22 includes the radially inward protruding pin 44 that tracks the grooves. As the groove is tracked, the plunger 22 rotates in the barrel and the user is unable to control rotation, due to the rotatable connection of plunger 22 and stem 26.

FIG. 2 is a perspective view of plunger 22 and FIG. 3 is a cross-sectional view of barrel 12. As shown in FIG. 3, pin 44 has a convex end 50. Pin 44 tracks fill groove 40 shown in FIG. 2. As a result of the convex end 50, when pin 44 is moved into a sloping portion of the track (i.e., a capture pocket), compression forces rather than shear forces act on pin 44.

FIG. 4 shows a partial, cut-away, cross-sectional view of plunger 22 in the region of groove 40. Groove 40 is on the exterior surface 42 of plunger 22. The groove includes a continuous cam side 43, a flat floor region 46, and a discontinuous cam side 50. The catch pockets defined on the discontinuous cam side 50 each are ramped along slope 48 and compress pin 44 to jam operation when other than programmed. Flat floor region 46 is adjacent continuous cam side 44 and sloping floor region 48 leads into the catch pockets on discontinuous cam side 50, as shown in FIGS. 2, 4 and 6.

FIG. 5 shows a plan view of the fill groove and drain groove, the circumference of plunger 22 being shown opened and flat. As used herein, the term "continuous cam side" refers to a side or sidewall surface of the groove wherein the pin and the plunger provide cam action over generally all of the longitudinal extent of the plunger. In contrast, the term "discontinuous cam side" refers to a side of the groove wherein cam action of the pin and the plunger is limited to defined longitudinal sections which can be separate spurs as in FIGS. 2 and 5, or areas of the track as in FIG. 8.

As clearly shown in FIG. 5, the discontinuous cam side 50 of filling groove 40 includes a plurality of pin stop regions or pockets, one of which is pin stop region 60. In the embodiment of FIG. 5, the pin stop region 60 is part of a generally U-shaped pin trap 62 which becomes shallower progressing away from track 40. As shown in FIG. 6 which is a partial, cut-away, cross-sectional view of region 62 from the perspective of section line 6'—6" in FIG. 2, pin trap 62 includes an ultimate pin stop wall 70 that is generally normal to trap floor 72. This provides a locking action of pin 44 within pin trap 62, but produces a shear force on the pin. Therefore, the bottom surfaces of pin trap 62 are preferably sloped relative to trap floor 72, due to sloping floor 48 of the groove 40 as seen in FIG. 4. The sloping floor jams pin 44 by compression, whereby pin 44, which is relatively thin, cannot be sheared off by forcing the plunger to move axially when pin 44 is locked in a catch pocket. Preferably stem 26 is arranged to buckle and the connection between stem 26 and plunger 22 is arranged to break, at a force less than that needed to shear off pin 44. To prevent excessive force on pin 44 when the plunger 22 is fully retracted such that pin 44 rests at the lowermost point on the plunger, stops 49 are provided to support the plunger in this position. Stops 49 are shown in FIG. 11.

The distance between pin stop 74 and pin stop 60 defines a limited travel distance $d_1$ that plunger 22 can move in barrel 12 when the plunger is moved in the prohibited direction $O_f$ as shown by arrow 76 in FIG. 5, whereupon operation is jammed. In contrast, pin 43 will travel on continuous cam surface 44 in direction F shown by arrow 78 substantially the entire longitudinal length of the fill tracking groove. During such travel, plunger 22 rotates relative to barrel 12. Movement in direction F extends the entire longitudinal length of continuous cam surface 44 due to the cam action of pin 44 on surface 43. If relative movement occurs in direction $O_f$, the plunger moves only distance $d_1$. As the plunger 22 rotates, pin 44 becomes successively aligned with each of the catch pockets in turn.

In the embodiment of FIG. 2, the fill groove circumscribes a longitudinal, angular or partial path about plunger 22. This spiral path spans a first arcuate portion of the plunger's circumference that, as shown in plan view FIG. 5, occupies arc $a_f$. The total circumference of plunger 2 is distance $a_t$. The drain tracking groove spans a second arcuate portion $a_d$. These arcuate portions can occupy the whole circumference, or only a part.

Trap region 62 in FIGS. 2 and 5 is generally U-shaped and includes a trap mouth between trap end wall 80 and trap end wall 82. When pin 44 is on the continuous cam side section between points 84 and 86, and the pin is moved with respect to the plunger in non-programmed direction $O_f$, the pin moves within the track substantially longitudinally parallel to longitudinally extending centerline C, that is, parallel to the axis of the plunger. The plunger and pin do not then act as a cam and cam follower, and the pin ultimately is trapped as it is compressed by the sloping floor 48 in trap region 62. By altering the number of trap regions, such as by increasing the number of trap regions, the syringe can be programmed to move a desired (e.g., very short) maximum distance d in directions opposite to the programmed direction F. The successive trap regions or pockets are spaced from one another by only a minimal distance such that the distance d between trap regions is inadequate for practical syringe use. Four to six traps are shown in the disclosed embodiments. The number of traps can be increased as necessary ten or even twenty traps being readily possible.

In FIG. 5, pin 44 is shown in the completely filled syringe position. Therefore, the pin has moved from pin position $P_1$ at the initiation point of the fill groove, traveled through that groove by co-acting with continuous cam side 43, rotated plunger 22 by span $a_f$ with respect to barrel 12, and resulted in expanding fluid chamber 18 until pin 44 is at position $P_2$ at the fully filled position of syringe 10.

The fill groove adjoins or has a confluence with the drain groove at an end of plunger 22 adjacent the fluid content chamber 18 of barrel 12. The confluence has a fill side 90 and a drain side 92. An imaginary line 91 defining the changeover from fill side 90 and drain 92 is offset with respect to longitudinal center line C by angle x. Fill continuous cam side 43 terminates at point 90 and the drain discontinuous cam side 110 initiates at that point. Similarly, fill discontinuous cam side 50 terminates at point 92 and drain continuous cam side 112 initiates at that point. Drain continuous cam side 112 includes an initial drain side region 114 that is longitudinally aligned with confluence fill side 90. That is, from the filled position when pin 44 moves through the confluence, it travels parallel to line C, strikes initial drain side region 114, and is guided into the drain track rather than back into the fill track, where pin 44 would become trapped. This guidance into drain track 42 is based upon the offset angle x between center line C and the imaginary confluence line 91 spanning confluence drain side 92 and confluence fill side 90. Thereafter, pin 44 follows continuous cam drain side 112 as long as plunger 22 moves relative to barrel 12 in direction D shown by arrow 120 to the left of FIG. 5. If the barrel moves in the opposite direction relative to the plunger, in direction Od shown by arrow 112, pin 44 leaves continuous cam drain side 112 and enters one of the plurality of trap regions on discontinuous cam drain side 110, which operate the same as those on the fill side. The cam action of pin 44 along continuous cam drain side 112 also rotates plunger 22 relative to barrel 12.

This rotation is enabled, in one embodiment, by a stem 124 shown in FIG. 7. In that embodiment, a plunger 126 has a hollow for receiving an enlarged stem stop 130 and the stem, inserted through stem port 128. In manufacturing, stem stop 130 is forced resiliently through stem port 128 or, alternatively, port 128 can be closed behind stop 130 after insertion. Heat is applied either to the inboard end of plunger 22 to close port 128 behind stop 130, and/or stem 124 to raise an accumulation of material forming stem stop 132 outside port 128. This enables stem 124 to be rotatable relative to plunger 126 but axially fixed thereto. Preferably, the axial strength of the stem and/or its connection to plunger 22 is less than the force needed to overcome locking of pin 44 in the trap pockets.

FIG. 11 illustrated an embodiment of the invention wherein stop means 49 are provided at the rear end of the barrel 12, for limiting the rear displacement of plunger 22 therein. Stop means 49, for example an inwardly protruding flange, is spaced from pin 44 such that as pin 44 reaches the end of travel of the confluence of track 40 and plunger 22 also abuts stop means 49. Therefore, the user cannot shear pin 44 off barrel 12 by exerting excessive pressure against pin 44 via said confluence.

Another embodiment as shown in FIG. 8 is characterized by a much narrower circumferential span defined by the fill and drain grooves. Therefore, it is possible (and recommended) to employ a plurality of pins 44 with corresponding fill and drain grooves around the circumference. Preferably the pins and their grooves are diametrically opposite, whereby compression on pins 44 in the trap pockets produces a symmetrical compression on the plunger.

Fill groove 160 is substantially similar to drain groove 162, and accordingly only drain groove 162 will be described in detail herein. Drain groove 162 includes continuous cam surface 164 and discontinuous cam surface 166. The discontinuous cam surface 166 includes pin stop regions 168. An imaginary longitudinal medial line M extending the length of drain tracking groove 162 is noted in FIG. 8. Continuous cam side 64 is subdivided into side sections, two of which are identified as side sections 170 and 172 in FIG. 8. During longitudinal or axial movement D in a drain mode, pin 44 crosses medial line M as shown by pin positions P3 and P4. Therefore, side sections of continuous cam side 64 are each angularly offset with respect to medial line M and cross that line. In the drain mode, if the plunger is moved with respect to the barrel in the non-programmed direction Od, the pin will track in groove 162 from position P4 to position P6. Thereafter, the pin will move in an exclusively longitudinal direction generally parallel to longitudinal axis C1 in FIG. 8. The pin thereafter will be stopped by compression due to a ramped bottom of the groove leading up to pin stop 176. Preferably two or more diametrically opposed pins are jammed at once. Further movement of the plunger relative to the barrel is precluded as pins 44 become jammed.

The final locations of pin 44, namely locations 182, are also arranged as traps. In FIG. 8, final trap 182 is the same as the other traps, including a trap ramp and trap stop face aligned under the terminal location of pin 44. In FIG. 5, the terminal trap can be the same as the other traps or wider than the other traps as shown. Preferably the terminal trap is also ramped.

As shown in FIGS. 9a, 9b, 10a and 10b, the pin can be arranged with a chamfered or a convex end to better engage the ramped floor 48 of pin traps 62 leading from track floor 72 to abutment 70 in plunger 22. FIGS. 9a and 9b show chamfered pin 45 as viewed looking into the trap 62 (FIG. 9a) and transversely thereof (FIG. 9b). FIGS. 10a and 10b illustrate convex pin 47 on similar views, with the successive positions of pin 47 shown in broken lines.

The syringe of the invention is truly non-reusable and not subject to manufacturing problems or possible actions to defeat the non-reuse features. Once the plunger is installed and cap 14 permanently affixed, the user has no means of access to the plunger to control its rotation. Therefore, only axial displacement of the plunger is possible, leading to the programmed motions and traps disclosed herein.

The claims appended hereto are meant to cover modifications and changes of the invention. For example, although a two tracking groove syringe is disclosed herein, it is equally possible to construct a single track syringe that enables the syringe to be filled by other mechanical means, that is, without utilizing the piston activity of plunger 22, and the plunger may then be programmed only to drain via a drain track groove. In contrast, the plunger may only include a fill track groove in order to fill fluid content chamber 18. This type of syringe may be useful in drawing blood. The claims appended hereto are meant to cover these and other modifications and changes.

What is claimed is:

1. A programmed action syringe comprising:
   a barrel having at least one pin protruding into a bore defined by said barrel;
   a plunger movable in either of two opposite directions along said bore, said plunger having, on its exterior, at least one tracking groove engaging the pin, the tracking groove defining a programmed path extending partly in at least a first longitudinal direction corresponding to at least one of said two opposite directions and partly in a direction transverse thereto, the tracking groove having a continuous cam side against which the pin can bear for unobstructed movement of the plunger in the first longitudinal direction and an opposing cam side blocking the pin and preventing any substantial movement of the plunger in an opposing second longitudinal direction, whereby plunger movement is constrained to follow the programmed path.

2. A programmed action syringe as claimed in claim 1 wherein said opposing cam side includes a plurality of pin stop regions, and wherein a longitudinal distance from the continuous cam side to a rear of each pin stop region defines a limited travel distance of said plunger with respect to said barrel in said second longitudinal direction.

3. A programmed action syringe as claimed in claim 1 including two tracking grooves respectively defining a fill groove and a drain groove is substantially opposite longitudinal direction said fill groove having a first continuous cam side for substantially complete longitudinal cam action in a fill direction and a respective opposing first discontinuous cam side, said fill direction being said first direction when said pin tracks said fill groove, said drain groove having a second continuous cam side for substantially complete longitudinal cam action in a drain direction and a respective second discontinuous cam side, said drain direction being said first direction when said pin tracks said drain groove, said fill and drain grooves having a confluence, near an end of said plunger adjacent a fluid content chamber of said barrel, at which said first continuous cam side terminates and adjoins an initiation of said second discontinuous cam side on a fill side of said confluence and at which said first discontinuous cam side terminates and adjoins an initiation of said second continuous cam side on a drain side of said confluence, said second continuous cam side having an initial drain side region longitudinally aligned with said fill side of said confluence such that said confluence is at an offset angle with respect to strict longitudinal travel of said pin through said confluence, and said pin strikes said initial drain side region during travel from said fill side through said confluence.

4. A programmed action syringe as claimed in claim 3 wherein said fill tracking groove circumscribes a longitudinal partial spiral path spanning a first arcuate portion of said plunger's circumference and said drain tracking groove circumscribes a longitudinal partial spiral path spanning a second arcuate portion of said plunger's circumference.

5. A programmed action syringe as claimed in claim 4 said first and second discontinuous cam sides include a plurality of pin stop regions, wherein the longitudinal distance between each pin stop defines a limited travel distance of said plunger with respect to said barrel in directions opposite said fill and drain directions respectively when said pin travels through said fill and drain grooves.

6. A programmed action syringe as claimed in claim 5 wherein said pin stop regions include U-shaped pin traps having trap entrances at the open end of the U-shape which are longitudinally aligned with sections of said first and second continuous cam sides such that longitudinal travel in a direction opposite said fill and drain directions respectively when said pin tracks said fill and drain grooves is non-rotational due to said pin entering said trap entrances.

7. A programmed action syringe as claimed in claim 6 wherein said fill and drain grooves each have a floor, a flat floor region thereof adjacent said continuous cam side having a depth substantially complementary to the protrusion of said pin into said barrel and the pin traps have a sloping floor region adjacent said discontinuous cam side having an increasing shallower depth as compared to said flat floor region, leading into the pin traps, whereby trapping of the pins causes compression of the pins.

8. A programmed action syringe as claimed in claim 6 wherein one end of said barrel includes means for mounting a needle thereon and the opposite end of said barrel being open, the syringe including a plunger stem protruding beyond the open end of said barrel, said plunger stem rotatively mounted to said plunger, thereby disabling rotative movement of said plunger relative to said barrel other than through cam action.

9. A programmed action syringe as claimed in claim 1 wherein said continuous cam side includes a plurality of continuous cam sections that are each angularly offset with respect to an imaginary longitudinal medial line extending through the length of said tracking groove such that said pin crosses said medial line a plurality of times during travel through said tracking groove.

10. A programmed action syringe as claimed in claim 9 wherein said discontinuous cam side includes a plurality of pin stop regions, wherein the longitudinal distance between each pin stop defines a limited travel distance of said plunger with respect to said barrel in said second longitudinal direction.

11. A programmed action syringe as claimed in claim 10 wherein said pin stop regions extend through said medial line.

12. A programmed action syringe as claimed in claim 11 wherein said pin stop regions are at a 90 degree or greater angle with respect to said medial line.

13. A programmed action syringe as claimed in claim 9 including two longitudinal tracking grooves respectively defining a fill groove and a drain groove, said fill groove having a first continuous cam side for substantially complete longitudinal cam action in a fill direction and a respective opposing first discontinuous cam side, said fill direction being said first direction when said pin tracks said fill groove, said drain groove having a second-continuous cam side for substantially complete longitudinal cam action in a drain direction and a respective second discontinuous cam side, said drain direction being said first direction when said pin tracks said drain groove, said fill and drain grooves having a confluence, near an end of said plunger adjacent a fluid content chamber of said barrel, at which said first continuous cam side terminates and adjoins an initiation of said second discontinuous cam side on a fill side of said confluence and at which said first discontinuous cam side terminates and adjoins an initiation of said second continuous cam side on a drain side of said confluence, said second continuous cam side having an initial drain side region longitudinally aligned with said fill side of said confluence such that said confluence is at an offset angle with respect to strict longitudinal travel of said pin through said confluence, and said pin strikes said initial drain side region during said travel from said fill side through said confluence.

14. A programmed action syringe as claimed in claim 13 wherein one end of said barrel includes means for mounting a needle thereon and the opposite end of said barrel being open, the syringe including a plunger stem protruding beyond the open end of said barrel, said plunger stem rotatably mounted to said plunger thereby disabling rotative movement of said plunger relative to said barrel other than through cam action of said pin.

15. A programmed action syringe as claimed in claim 9 wherein said tracking groove has a floor, a flat floor region thereof adjacent said continuous cam side having a depth substantially complementary to the protrusion of said pin into said barrel and a sloping floor region thereof defining said pin traps adjacent said discontinuous cam side, the pin traps having an increasing shallower depth as compared to said flat floor region.

16. A programmed action syringe as claimed in claim 9 wherein one end of said barrel includes means for mounting a needle thereon and the opposite end of said barrel being open, the syringe including a plunger stem protruding beyond the open end of said barrel, said plunger stem rotatably mounted to said plunger thereby disabling rotative movement of said plunger relative to said barrel other than through cam action of said pin.

17. A programmed action syringe as claimed in claim 16 wherein said plunger stem has a shear strength less than a shear strength of said pin.

18. A programmed action syringe comprising:
a barrel having at least one pin protuding into a bore of said barrel;
a plunger adapted to travel through said bore, said plunger having, on its exterior surface, at least one longitudinal tracking groove having a continuous cam side for unlimited cam action travel of said pin in said groove in a first longtiudinal direction and an opposing discontinuous cam side for limited cam action travel in an opposing second longitudinal direction, the discontinuous cam side including a plurality of pin stop regions, a longitudinal distance defined by each pin stop region defining a limited travel distance of said plunger relative to the barrel in said second longitudinal direction, said tracking groove circumscribing a longitudinal, at least partly spiral path about said plunger, causing said plunger to rotate relative to said barrel during longitudinal travel in said first direction of said pin through said bore.

19. A programmed action syringe as claimed in claim 18 wherein said pin stop regions include U-shaped pin traps.

20. A programmed action syringe as claimed in claim 19 wherein said U-shaped pin traps include trap entrances at the open end of the U-shape which are longitudinally aligned with sections of said continuous cam sides such that longitudinal travel in said second direction of said plunger is non-rotational due to said pin entering said trap entrances.

21. A programmed action syringe as claimed in claim 20 wherein said tracking groove has a floor, a flat floor region thereof adjacent said continuous cam side having a depth substantially complementary to the protrusion of said pin into said barrel and wherein at least some of the pin traps have a sloping floor region beginning at said discontinuous cam side and having an increasing shallower depth leading into the pin traps as compared to said flat floor region.

22. A programmed action syringe as claimed in claim 20 wherein one end of said barrel includes means for mounting a needle thereon and the opposite end of said barrel being open, the syringe including a plunger stem protruding beyond the open end of said barrel, said plunger stem rotatably mounted to said plunger thereby disabling rotative movement of said plunger relative to said barrel other than through cam action of said pin in said longitudinal spiral path groove.

23. A programmed action syringe as claimed in claim 22 wherein said plunger stem has a shear strength less than a shear strength of said pin.

24. A programmed action syringe as claimed in claim 22, wherein a plurality of said pins and said grooves are disposed circumferentially around the syringe.

25. A programmed action syringe as claimed in claim 24, wherein at least some of said pins and said grooves are arranged in diametrically opposed pairs.

26. A programmed action syringe comprising:
a barrel having at least one pin protruding into a bore of said barrel;
a plunger movable longitudinally through said bore for at least one of filling and emptying the syringe, said plunger having on its surface at least one tracking groove receiving the pin and defining a path proceeding partly longitudinally and partly transversely, the plunger being received in the barrel such that user control of relative displacement of the plunger in the barrel is limited to exertion of relative force between the plunger and the barrel in longitudinal directions, the tracking groove having unobstructed surfaces engageable against the pin on one side of said tracking groove for unlimited travel of said plunger relative to said barrel in a permitted longitudinal direction along the path, and the tracking groove having opposing obstructed surfaces on a second side of said tracking groove for capturing said pin and blocking travel of the plunger in a direction opposite to said permitted longitudinal direction, whereby plunger movement is constrained to follow a path along the permitted longitudinal direction.

* * * * *